United States Patent
Saxena et al.

(10) Patent No.: US 8,685,241 B1
(45) Date of Patent: Apr. 1, 2014

(54) AXIAL AND RADIAL FLOW COLUMNS WITH INFLATABLE SEALS TO FACILITATE PACKING AND UNPACKING

(71) Applicant: Sepragen Corporation, Hayward, CA (US)

(72) Inventors: Vinit Saxena, Pleasanton, CA (US); Renu Saxena, Pleasanton, CA (US); David Zuffi, Rohnert Park, CA (US)

(73) Assignee: Sepragen Corporation, Hayward, CA (US)

( * ) Notice: Subject to any disclaimer, the term of this patent is extended or adjusted under 35 U.S.C. 154(b) by 0 days.

(21) Appl. No.: 13/723,959

(22) Filed: Dec. 21, 2012

Related U.S. Application Data

(60) Provisional application No. 61/578,615, filed on Dec. 21, 2011.

(51) Int. Cl.
*B01D 15/08* (2006.01)

(52) U.S. Cl.
USPC ........................................ 210/198.2; 210/656

(58) Field of Classification Search
USPC ......... 210/635, 656, 657, 659, 198.2; 96/101, 96/105, 106; 141/12, 80
See application file for complete search history.

(56) References Cited

U.S. PATENT DOCUMENTS

| | | |
|---|---|---|
| 4,627,918 A | 12/1986 | Saxena |
| 4,833,083 A | 5/1989 | Saxena |
| 4,840,730 A | 6/1989 | Saxena |
| 4,865,729 A | 9/1989 | Saxena |
| 5,041,216 A | 8/1991 | Henzler et al. |
| 5,057,428 A | 10/1991 | Mizutani et al. |
| 5,187,095 A | 2/1993 | Bliem et al. |
| 5,256,298 A | 10/1993 | Powell |
| 5,376,548 A | 12/1994 | Matsuo et al. |
| 5,429,746 A | 7/1995 | Shadle et al. |
| 5,462,659 A | 10/1995 | Saxena et al. |
| 5,571,720 A | 11/1996 | Grandics et al. |
| 5,667,676 A * | 9/1997 | Alaska ................. 210/198.2 |
| 5,714,074 A * | 2/1998 | Karlsson et al. ............ 210/656 |
| 5,976,870 A | 11/1999 | Park |
| 6,139,732 A * | 10/2000 | Pelletier ................. 210/198.2 |
| 6,576,201 B1 | 6/2003 | Woo et al. |

(Continued)

FOREIGN PATENT DOCUMENTS

WO    WO 2008/009412    1/2008

OTHER PUBLICATIONS

Article, "World'S Tallest High Performance Radial Flow Chromatography (HP-RFC) Column", 2 pages, Published May 4, 2010 on www.proxcys.com.

(Continued)

*Primary Examiner* — Ernest G Therkorn
(74) *Attorney, Agent, or Firm* — Rutan & Tucker, LLP

(57) ABSTRACT

A method, apparatus, and system are described to pack and unpack resin in a chromatography-column. One or more inflatable seals are deflated to pack a resin slurry from a bottom outlet valve into a resin bed chamber located between an outer shell of the column and an inner frit of the chromatography-column. The resin slurry is pumped into and through an outlet packing-and-running port and passed one or more deflated inflatable seals to pack the resin bed to a designated pressure with resin slurry. The inflatable seals are inflated to seal the resin bed in place.

1 Claim, 9 Drawing Sheets

(56) References Cited

U.S. PATENT DOCUMENTS

| | | |
|---|---|---|
| 6,844,187 B1 | 1/2005 | Wechsler et al. |
| 6,979,308 B1 | 12/2005 | MacDonald et al. |
| 7,033,823 B2 | 4/2006 | Chang |
| 7,163,825 B2 | 1/2007 | Gault |
| 7,578,934 B2 * | 8/2009 | Gill et al. .................. 210/198.2 |
| 7,682,505 B2 * | 3/2010 | Vidalinc .................. 210/198.2 |
| 7,972,506 B2 * | 7/2011 | Hofmann .................. 210/198.2 |
| 2003/0102266 A1* | 6/2003 | Ritacco ........................ 210/656 |
| 2004/0058434 A1 | 3/2004 | Gault |
| 2007/0134790 A1 | 6/2007 | Gould et al. |
| 2007/0193933 A1* | 8/2007 | Vidalinc .................. 210/198.2 |
| 2007/0199899 A1* | 8/2007 | Alaska ........................ 210/659 |
| 2009/0071888 A1 | 3/2009 | Raedts |
| 2010/0193441 A1* | 8/2010 | Agee et al. .................... 210/656 |

OTHER PUBLICATIONS

Article, "Isocratic Sanitary Packing & Running System", 2 pages, Retrieved Dec. 21, 2012 on http://www.proxcys.com/index.php?option=com_content&view=article&id=84&Itemid=98.

Phillips & Signs, "Current Protocols in Protein Science", Unit 4.4, 2004, pp. 4.4.1-4.4.15.

Levison, P. (J. Chromal. B 2003, 790:17-33).

* cited by examiner

AXIAL AND RADIAL FLOW COLUMNS WITH INFLATABLE SEALS TO FACILITATE PACKING AND UNPACKING

RELATED APPLICATIONS

This application claims the benefit of under 35 USC 119(e) and incorporates in by reference the substance of U.S. provisional patent application Ser. No. 61/578,615, titled "Axial and radial flow columns with inflatable seals to facilitate packing and unpacking", filed Dec. 21, 2011.

FIELD OF THE INVENTION

An aspect of an embodiment of the invention generally relates to columns used in the production of product of interest and cyclically harvesting the product.

BACKGROUND OF THE INVENTION

Today, biological proteins are made in bioreactors by growing secretor cells. The bioreactors may be a large, voluminous, stirred tank/bag design where the cells are grown.

SUMMARY OF THE INVENTION

Various methods and apparatuses are described for a chromatography-column. The chromatography-column may have one or more inflatable seals, a first port, and a second port to facilitate packing and unpacking resin in the chromatography-column. The packing and unpacking of resin in the chromatography column is designed to occur using the first port and the second port and controlling the inflation state of the one or more inflatable seals. The same two ports are also used during a normal operation of the chromatography-column by running product of interest in and through these two ports to have the resin packed in the chromatography column filter the product of interest. The one or more inflatable seals within the chromatography-column block or unblock a pathway to the resin bed in the chromatography-column.

BRIEF DESCRIPTION OF THE DRAWINGS

The drawings refer to embodiments of the design.

Figure 1:
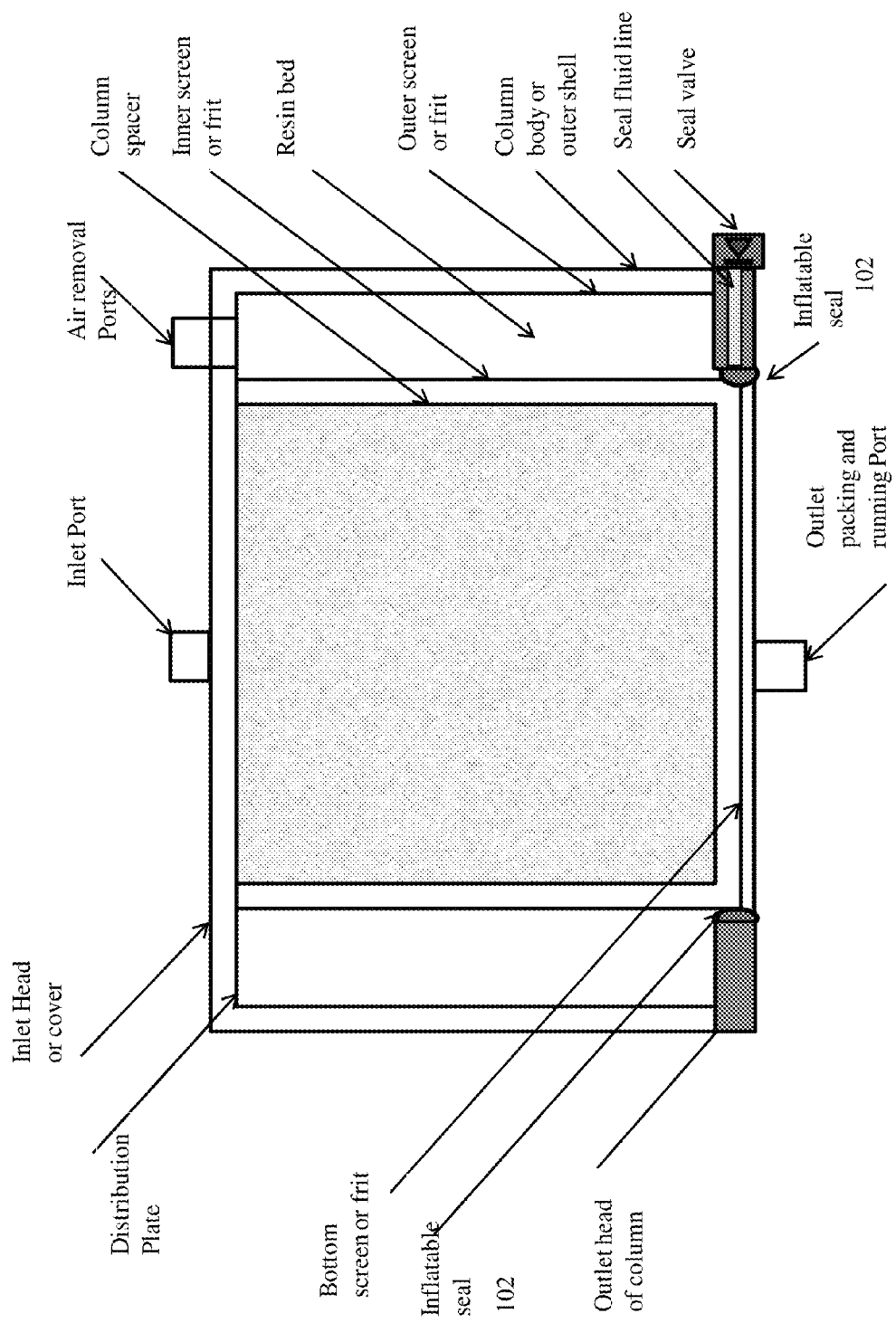
FIG. 1 illustrates a radial-flow chromatography-column with one or more inflatable seals for packing and unpacking resin in the column.

While the invention is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the invention.

DETAILED DISCUSSION

In the following description, numerous specific details are set forth, such as examples of specific frits, named components, connections, types of columns, etc., in order to provide a thorough understanding of the present invention. It will be apparent, however, to one of ordinary skill in the art that the present invention may be practiced without these specific details. In other instances, well known components or methods have not been described in detail but rather in a block diagram in order to avoid unnecessarily obscuring the present invention. Further specific numeric references such as first pump, may be made. However, the specific numeric reference should not be interpreted as a literal sequential order but rather interpreted that the first pump is different than a second pump. Thus, the specific details set forth are merely exemplary. The specific details may be varied from and still be contemplated to be within the spirit and scope of the present invention.

FIG. 1 illustrates a radial-flow chromatography-column with one or more inflatable seals for packing and unpacking resin in the column. The radial-flow chromatography-column includes components such as an inlet port, an outlet packing-and-running port located at the bottom of the chromatography-column for easy drainability, one or more inflatable seals, each with a seal fluid line and seal valve, a body and outer shell of the column, the column's distribution plate, a bottom screen or frit, an inner screen or frit, an outer screen or frit, a resin bed chamber located between the inner screen and the outer shell of the column, and an air vent coupled to the resin bed chamber. The chromatography-columns may be axial and/or radial flow columns with the inflatable seals 102 to facilitate packing and unpacking of resin in the column. The chromatography-column can be a radial-flow chromatography-column in one embodiment or an axial-flow chromatography-column in another. In the radial-flow chromatography-column, the inflatable seal is located against the inlet frit if packing from the bottom.

The chromatography columns have columns with resin that are connected downstream of a bioreactor. The product of interest coming from 1) the bioreactor, 2) a protein solution from another tank, or 3) a synthetic product of interest from another tank, or 4) any of these bonds/adsorbs via ion-exchange, affinity or hydrophobic interaction with the resin in the chromatography column. The chromatography column can pack and unpack the resin using the same inlet and outlet ports that are used while running the chromatography column. These packing and unpacking operations are facilitated by using one or more inflatable seals, which retains the resin while the column is in the "run" or "operational" mode. In general, the method to pack and unpack resin in the chromatography-columns differs from some other because it only uses the inlet and outlet valves of the chromatography-columns and one or more inflatable seals 102 within the chromatography-column to block or unblock the pathway to the resin bed in the chromatography-column.

In general, the radial-flow chromatography-columns has merely one inlet port and one outlet port, which are used both 1) in normal operation of the chromatography-column for product of interest in and out of the chromatography-column as well as 2) packing/unpacking of resin in and out of the chromatography-column (i.e.—no separate packing/unpacking port(s) are needed). There is no dead area under the resin bed that cannot be cleaned out or requires extensive flushing. The outlet port is below the resin bed and not in the collector rod which is not drainable. The bottom of the chromatography-column has a slope to facilitate drainablity. The top head bottom plate has a slope outward to facilitate air removal.

In general in the axial-flow chromatography-columns, the chromatography-column has merely one inlet port and one outlet port a retractable valve, a top frit, a bottom frit, and the one or more inflatable seals. The chromatography-column is packed via the retractable valve that penetrates either the top or bottom frits when the retractable valve is in an insertion position, and then a slurry of resin can be pumped into the chromatography-column passed the inflatable seals, and when the retractable valve is retracted it seals off the frit opening and allows only the fluid traversing through the resin bed and exiting the frit to go through the outlet or inlet port during normal operations. In this design, the inflatable seal when deflated creates a passage on the outside of the distributor or frit for the resin to be pumped into the column chamber. Once packed to the desired pressure, the frit is energized or inflated to seal the resin in the bed between the frits and the chromatography-column can be run in forward or reverse flow with the resin bed intact. When the chromatography-column has to be un-packed and the resin discharged, the seal is deflated and buffer pumped from the opposite direction. The bed then slurries and discharges out of the opening created by the seal.

Figure 2:
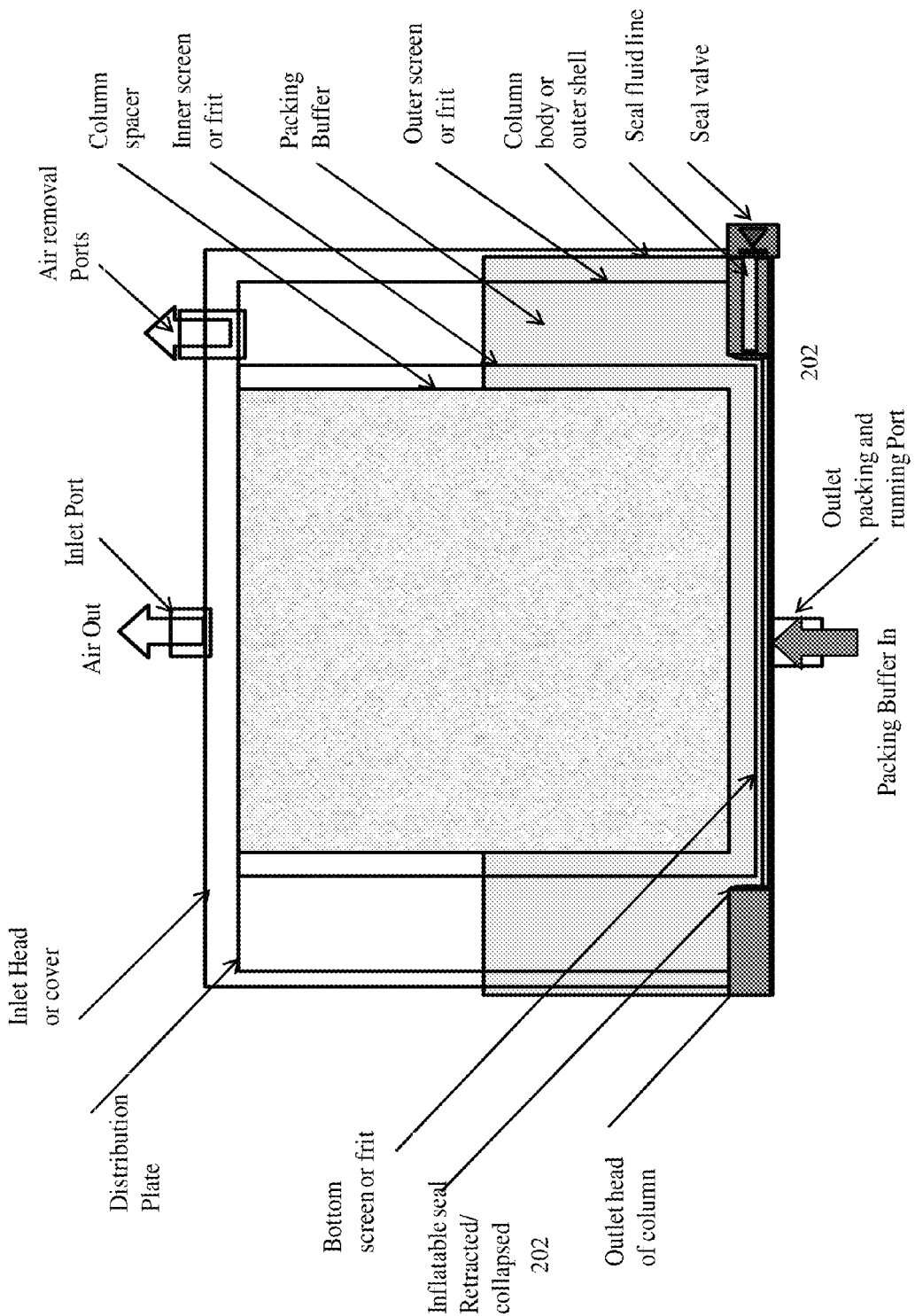
FIG. 2 illustrates a radial-flow chromatography-column with one or more inflatable seals currently deflated to allow a step of priming and air removal of the chromatography-column during packing of the resin bed.

FIG. 2 illustrates a radial-flow chromatography-column with one or more inflatable seals currently deflated to allow a step of priming and air removal of the chromatography-column during packing of the resin bed.

The packing skid can consist of a pump with a multi-port switchable inlet valve which can be connected to the resin slurry, buffer and/or a testing solution like salt water or acetone. The pump on the downstream side of method is connected to a pressure gauge, a bubble trap and through two 4-port 2-way valves to the chromatography-column. Initially, the column valves are set so that buffer is pumped into the chromatography-column and air is displaced out of the chromatography-column from the inlet which is directed back into the slurry line.

The chromatography-column may be packed easily by following the steps that follow. First, make a slurry of the packing in an equilibration buffer. With both inlet and outlet valves open and slurry packing seal 202 deflated, pump the equilibration buffer from the buffer container in the resin bed of the chromatography-column and recirculate until all the air is removed. Pack the buffer solution into the chromatography-column to remove air and then close the air vent.

Figure 3A:
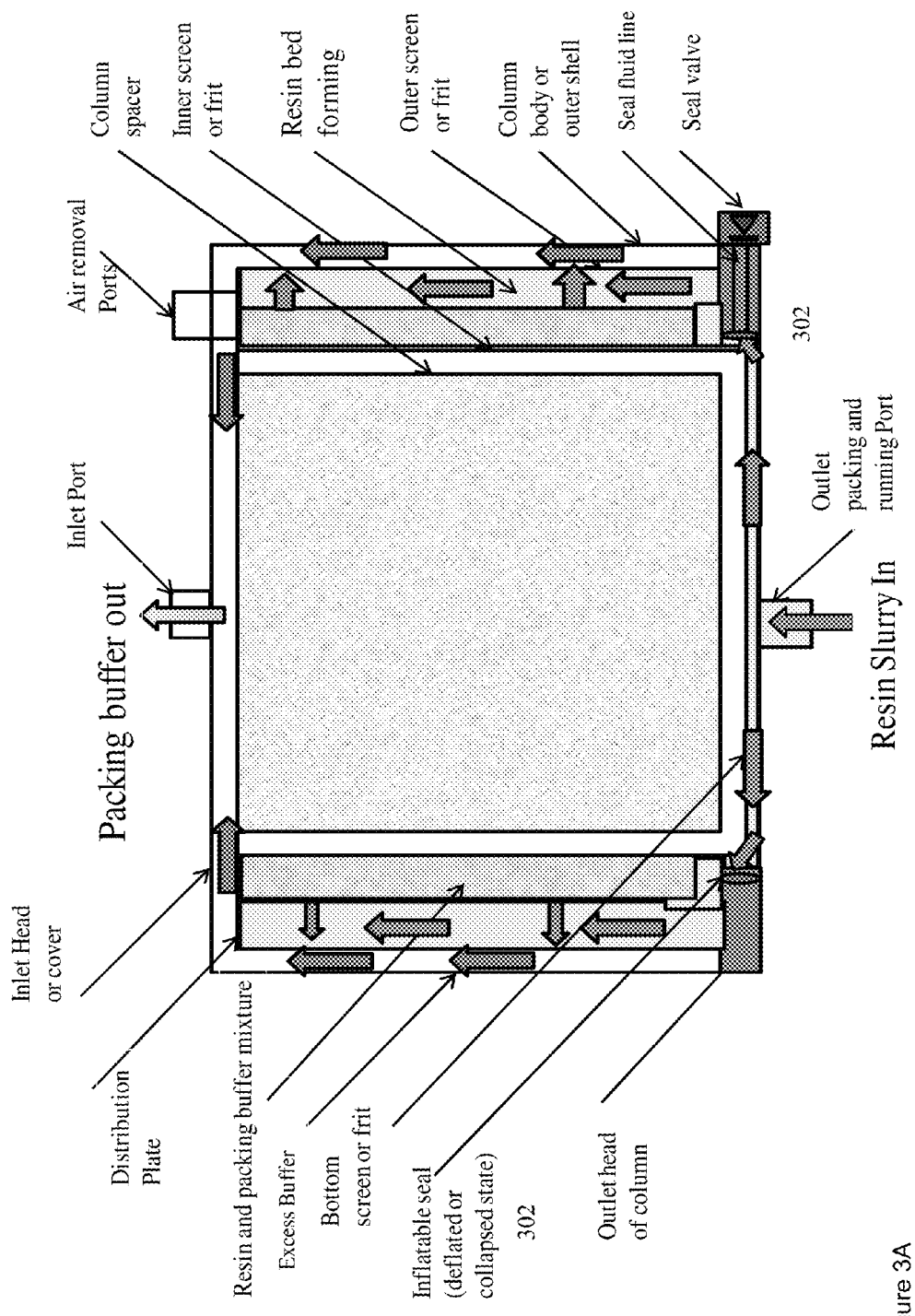
FIGS. 3A and 3B illustrate a radial-flow chromatography-column with one or more inflatable seals currently collapsed for packing resin slurry from the bottom outlet valve into the resin bed chamber located between the outer shell of the column and the inner frit of the chromatography-column.
Figure 3B:
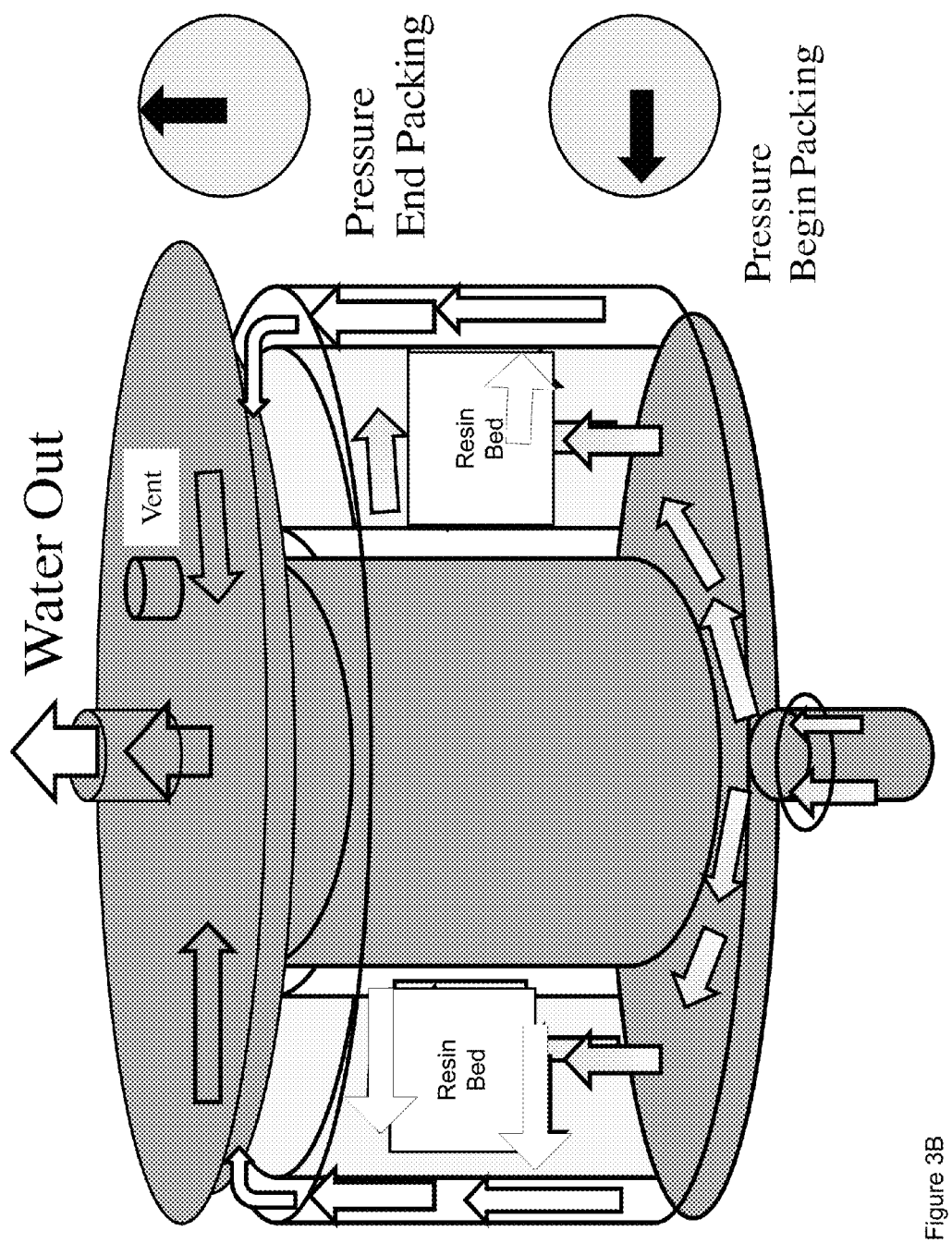

FIGS. 3A and 3B illustrate a radial-flow chromatography-column with one or more inflatable seals currently collapsed for packing resin slurry from the bottom outlet valve into the resin bed chamber located between the outer shell of the column and the inner frit of the chromatography-column. A second frit may be between the outershell and the resin bed. Thus the resin bed is between the two frits as well.

Overall, a pump pumps resin slurry into and through the outlet packing-and-running port/connection to pack the resin bed to a designated pressure with resin slurry and then automatically stop the pump and expand the inflatable seal mechanism. Specifically, the pump packs the slurry of resin via the outlet port to the deflated inflatable packing seal and then into the column resin bed chamber. Excess buffer solution from the priming step will now get displaced from the chromatography-column as the resin bed compacts against the top frit and extends downwards. The pressure will gradually rise inside the column and when the chromatography-column is fully packed with resin and no voids exist, then the pressure rise will suddenly accelerate until the desired resin compaction. The chromatography-column is now packed with resin. The next step is to close column inlet and outlet valves coupled to the respective ports. The next step is to inflate the inflatable packing seals 302 and close the packing seal inflation valve.

Thus, with the inflatable seals 302 still deflated, the resin slurry can be pumped in from the column outlet port (after the column has been primed) until the desired packing pressure or bed compaction. Thereafter, the inflatable seals 302 are inflated and the resin bed is sealed off. Excess resin in the area below the seals 302 are easily discharged from the column outlet port by pumping the buffer solution through the column inlet port and letting the excess slurry in the bottom chamber below the bottom frit run out the outlet port.

Once the chromatography-column is primed, the slurry port is engaged. Next, the resin slurry is pumped into the column chamber from the bottom. When fully packed to the desired pressure, the inflatable seal is energized/inflated. The slurry line is then rinsed by pumping buffer through the column bypass line back into the slurry tank. Once clean buffer is now pumped into the top of the chromatography-column and excess resin below the inflatable seal is removed from the chromatography-column by pumping the buffer into the chromatography-column from the top and removing unpacked resin from the bottom outlet into the slurry tank.

Figure 4A:
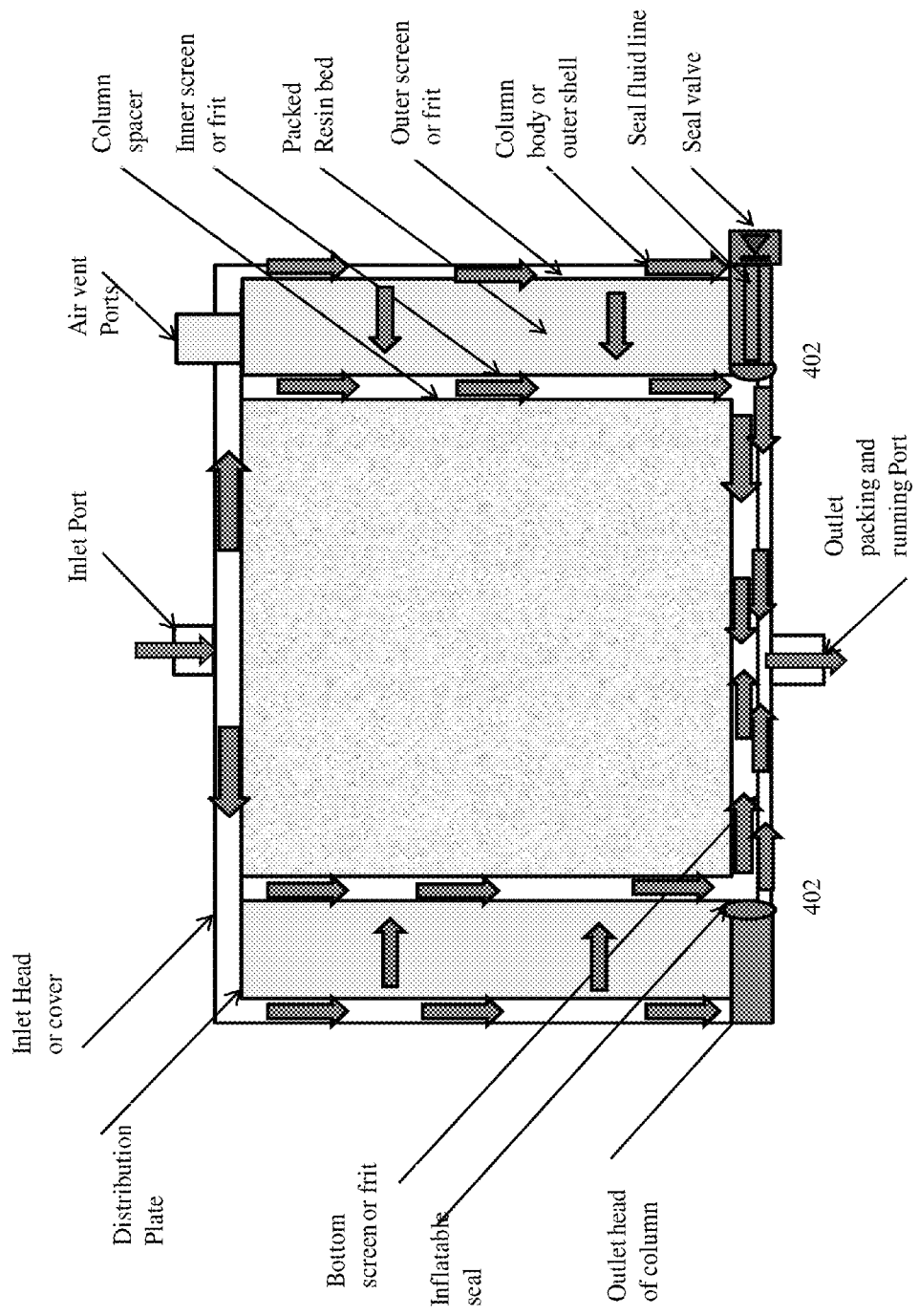
FIGS. 4A and 4b illustrate a radial-flow chromatography-column with one or more inflatable seals currently expanded under normal forward flow operation to retain the resin bed.
Figure 4B:
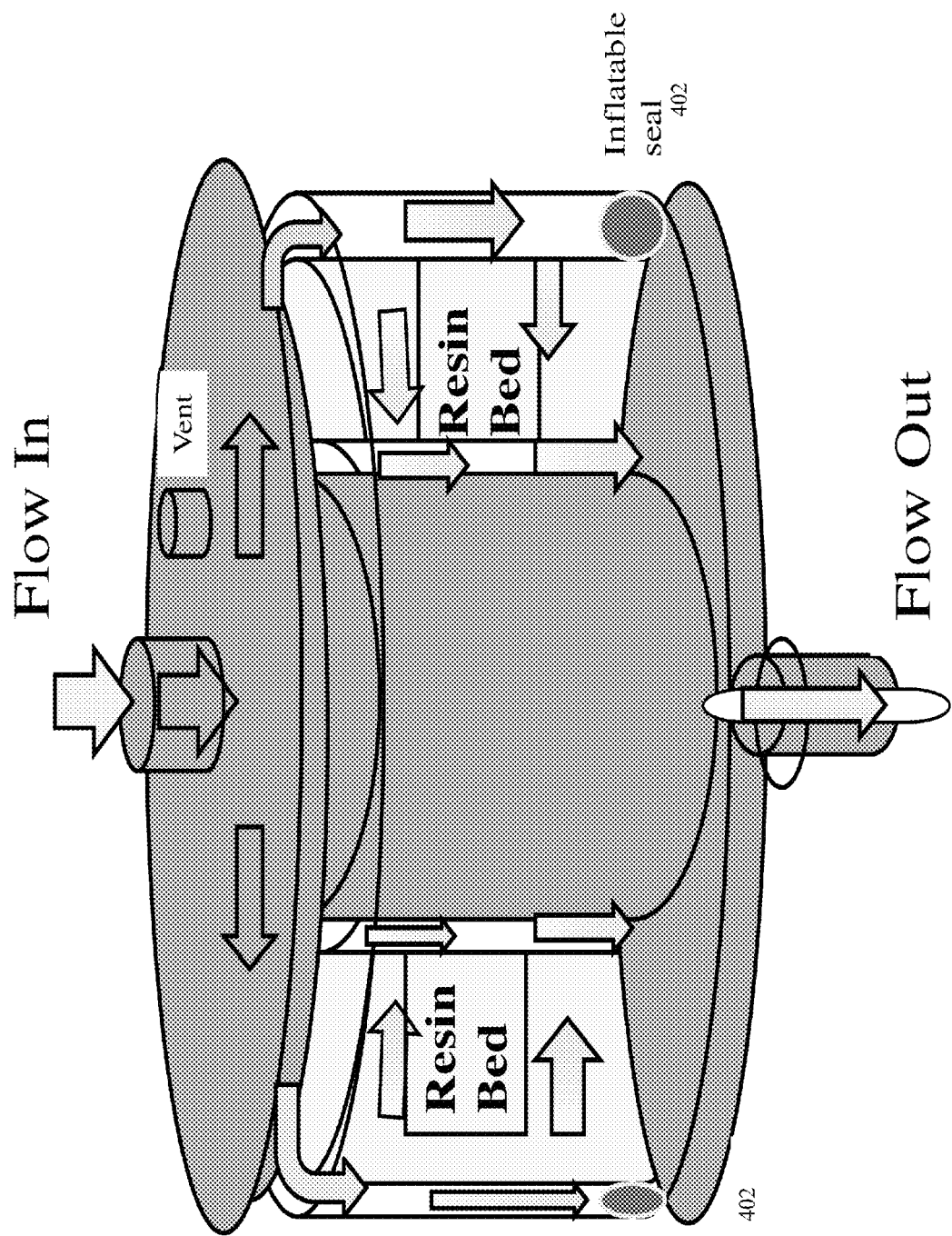

FIGS. 4A and 4B illustrate a radial-flow chromatography-column with one or more inflatable seals currently expanded under normal forward flow operation to retain the resin bed. As discussed, once the column is packed and the inflatable seals 402 are inflated, then one can clean out residual resin not packed between an inflated seal and a top frit. The chromatography-column is now ready for normal operation. As discussed, the one or more chromatography-columns have columns with resin that are connected downstream of the bioreactor. The product of interest from the bioreactor bonds/adsorbs via ion-exchange, affinity or hydrophobic interaction with the resin. The chromatography-column uses the inflatable seals 402 to retain the resin while the chromatography-column is in the "run" or "operational" mode.

Figure 5:
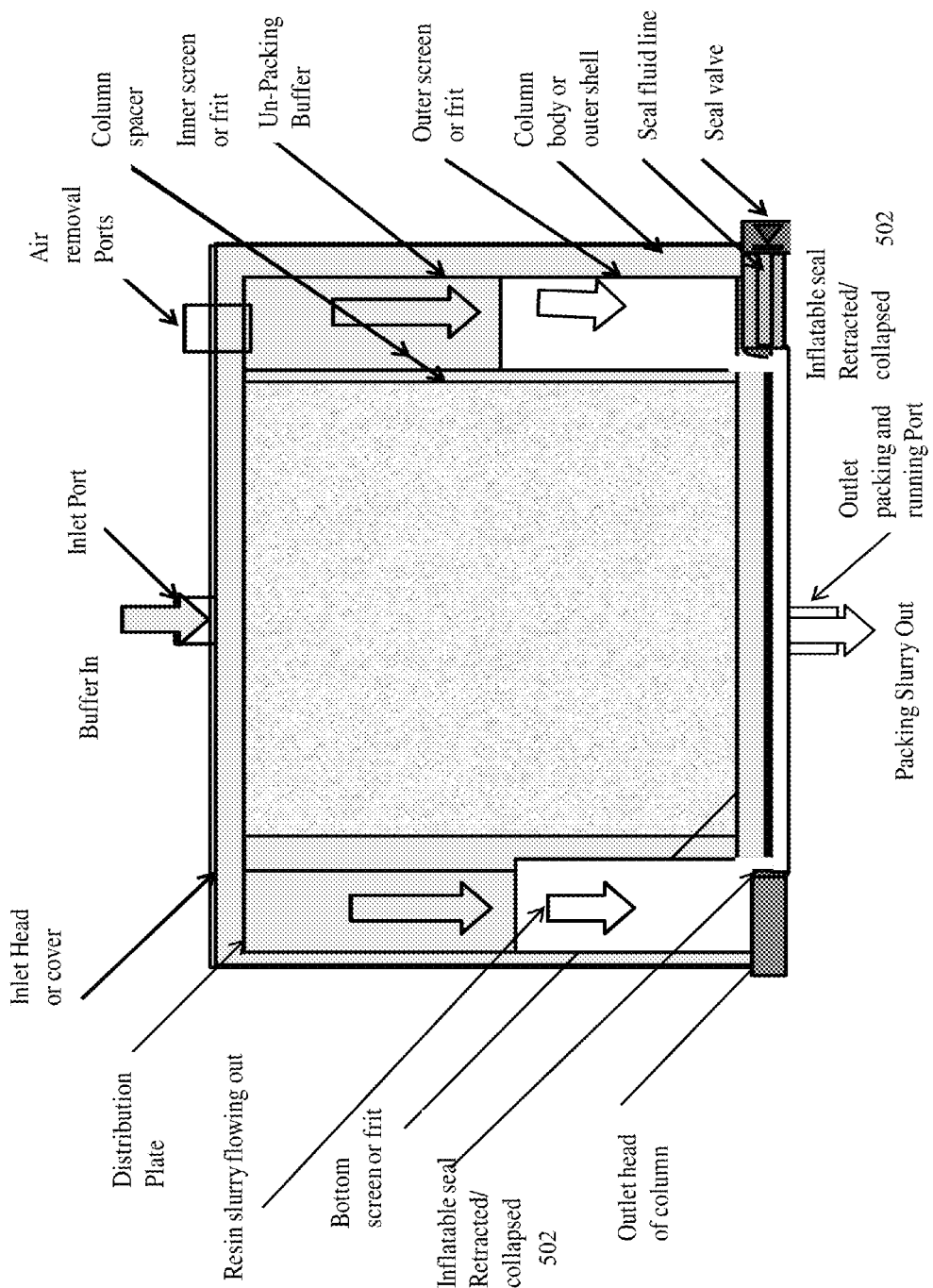
FIG. 5 illustrates a radial-flow chromatography-column with the one or more inflatable seals deflated to unpack resin from the chromatography-column.

FIG. 5 illustrates a radial-flow chromatography-column with the one or more inflatable seals deflated to unpack resin from the chromatography-column. The column with the seals 502 is easily packed and unpacked with resin in the column using the same two ports for normal operation running of product of interest in the bioreactor and packing resin into the chromatography-columns that filter the product of interest. Once the inflatable seals 502 are deflated, then the resin can be pumped out of the chromatography column as a slurry for storage.

Unpacking of the resin is also accomplished by pumping buffer from the inlet port but with de-energizing or deflating the seals. The resin bed slurries and flows out the column outlet port. This procedure can be programmed into a controller and easily automated for reproducible packing requiring little manual intervention.

In some cases, the bed may have settled and a buffer head may be detected on top of the resin bed. In such cases the bed adjuster may need to be lowered to the resin surface. (Before doing this be sure that there is no pressure in the line.)

a) Now reduce the pressure in the top adjuster seal by opening the air valve.

b) If course adjustment is needed use the Unlock Button and then move the adjuster down. If only a fine adjustment is needed, use the hand-wheel.

c) Once in place, re-inflate the adjuster seal up to 50 psi and close the valve.

d) Run the chromatography-column in the forward and reverse direction at max flow for 3-5 bed volumes to condition the bed.

e) The chromatography-column is now ready for a packing integrity test and operation.

Unpacking the Chromatography-Column

The Chromatography-column may be unpacked in 5 easy steps.

a) Deflate the bottom inflatable packing seals.

b) Now pump water or packing buffer at high flow rate through top (inlet port) of the chromatography-column.

c) The resin will form a slurry and exit the outlet port.

d) Remove inlet tubing from water/buffer and pump air on to the bed (the air will disrupt bed) and then pump water again.

e) Repeat these steps until all resin is out and only water is seen f) Displace the water by pumping air until all water is out.

g) The chromatography-column is now unpacked.

Note: In some cases, over time, the resin hardens as a cake and all resin may not be easily removed by following the above mentioned procedure. In such a case, remove the bottom flow adapter. Put water in the chromatography-column and manually with a spatula or similar mechanism stir and disrupt the bed and pour the resin out from the chromatography-column into a container. Also wash resin from the bottom adapter. Let dry.

Figure 6:
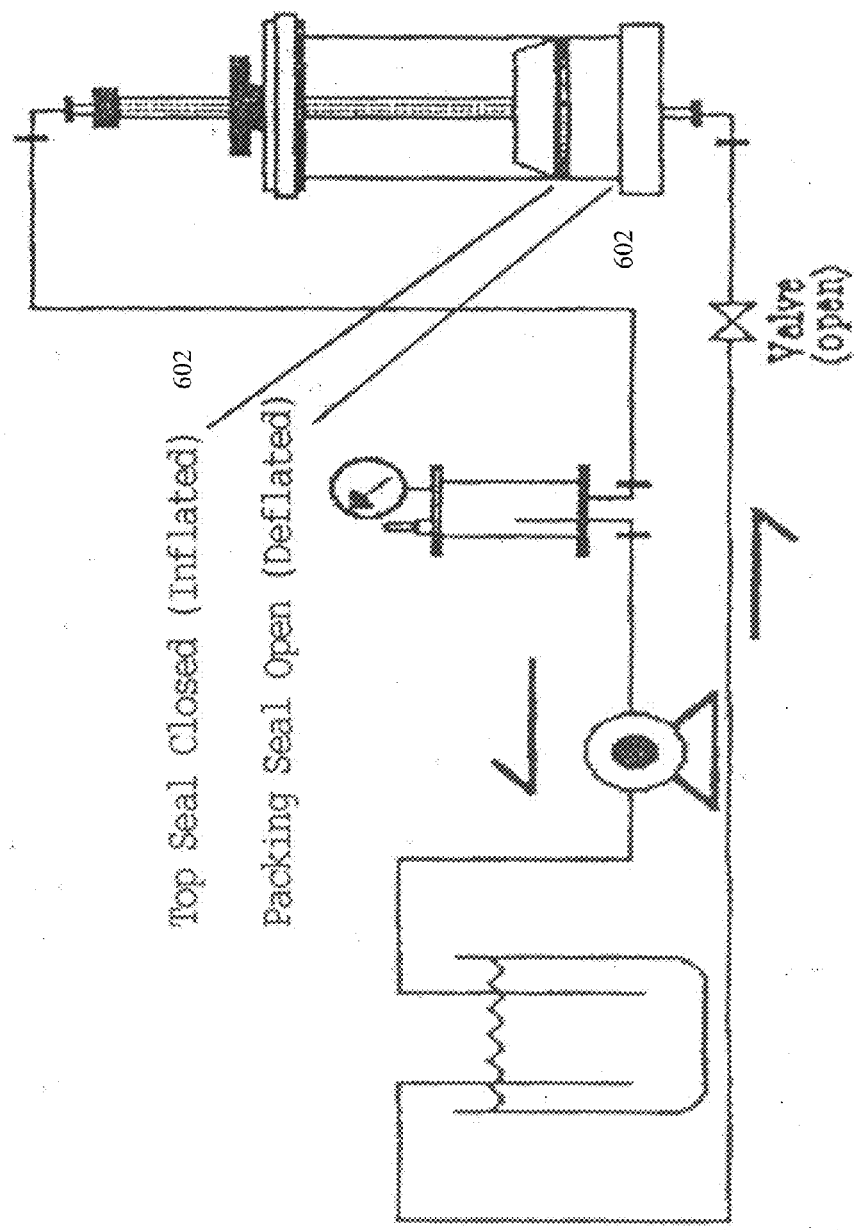
FIG. 6 illustrates a chromatography-column with one or more inflation/deflation packing seals.

FIG. 6 illustrates a chromatography-column with one or more inflation/deflation packing seals. The column can include inlet and outlet connections, chromatography media (resin), packing buffer solution, and equilibration buffer. The chromatography-column couples to a valve or tubing pinch as well as a variable speed pump with forward/reverse flow control, and a pressure gauge, glycerin filled, 0 to 30 or 60 psig.

The cavity under the outlet frit is connected on the outside of the flow adapter to the column chamber. The passage has one or more inflatable seals. When the seals 602 are not inflated (energized), the resin chamber is contiguous with the column outlet and resin slurry may be pumped in or out of the column bypassing the frit. Once the seals 602 are inflated or energized, the path is closed and flow can only go through the bottom frit while the resin is retained by the frit.

On the outside of the Adjuster is a "Flow adapter inflatable seal". When the adjuster is at the desired height and the threaded rod is "locked in place", the inflatable seal is inflated by directing pneumatic air pressure to the seal by opening the "flow adapter seal inflation valve", inflating the seal once the pressure has reached 50 psi and then closing the valve. When the column is NOT under pressure and there is no flow through the column, the seal may be deflated by opening the "flow adapter seal inflation valve" to the atmosphere, i.e., without air connected. The adjuster may now be moved up or down by using the quick release nut assembly.

Packing the Chromatography-Column

Figure 7:
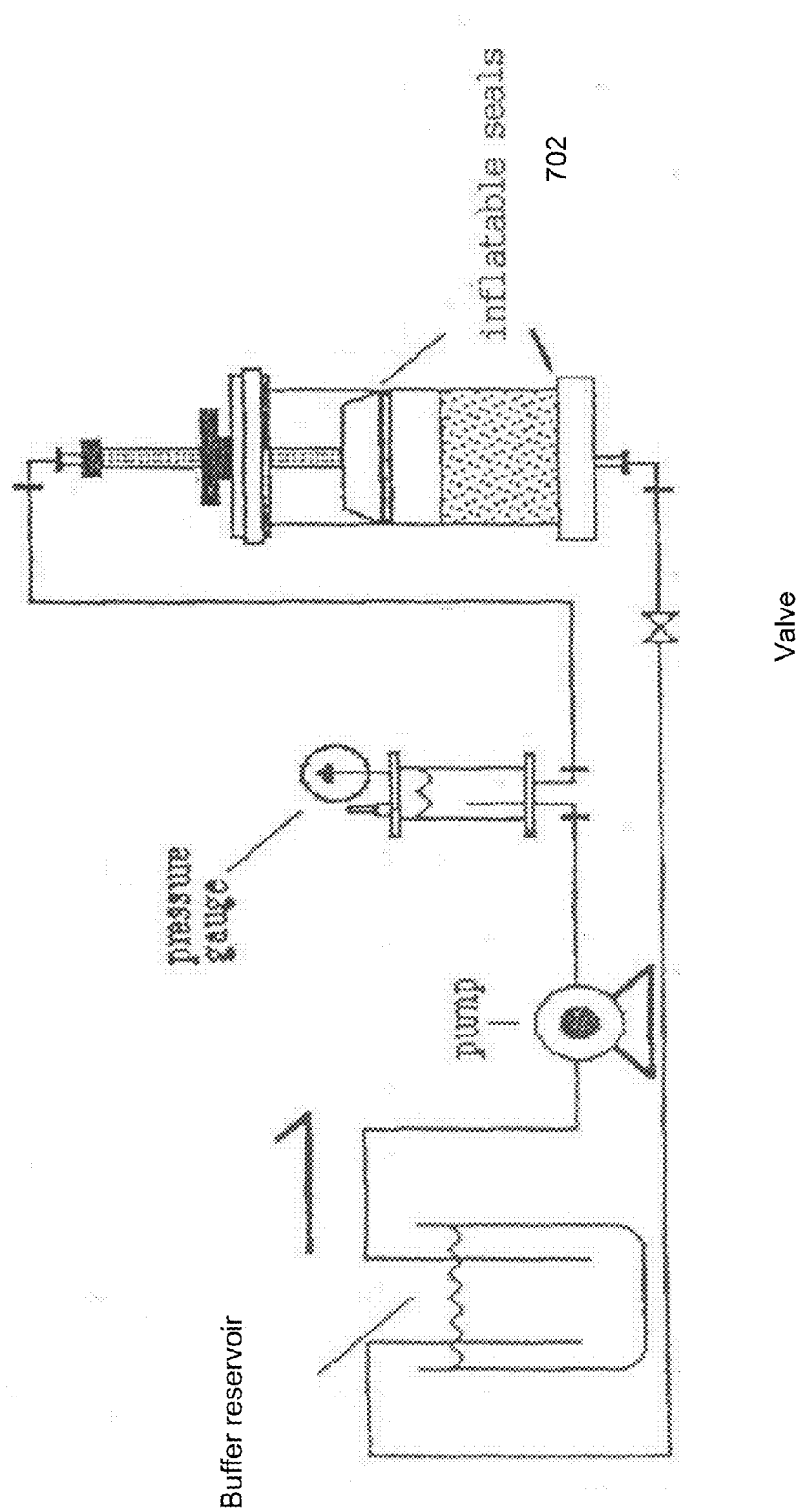
FIG. 7 illustrates a chromatography-column with one or more inflation/deflation packing seals being packed with resin.

In one embodiment, the chromatography-column may be packed with resin as follows. Connect the packing slurry and buffer containers to the column via the pump and pressure gauge (with guard) and inlet and outlet valves as shown in FIG. 7. The chromatography-column may be packed easily by following the steps below:

a) First make 30-50% slurry of the packing in equilibration buffer. Use 20-25% more slurry than the calculated volume of the bed, allowing for bed compaction, hold-up in the lines and wastage.

b) Next set up the column with the adjuster to the desired bed height and lock the adjuster. Inflate the top flow adapter seal and close the valve.

c) Set the pump flow rate at 10-20% more than the operating flow-rate. With both inlet and outlet valves open and slurry packing seal Deflated, pump buffer from the buffer container and recirculate until all the air is removed.

d) Pump packing slurry via the column outlet passed the deflated slurry packing seal into the column chamber Excess buffer will now get displaced from the column as the resin bed compacts against the top frit and extends downwards. The pressure will gradually rise and when the column is fully packed the pressure rise will suddenly accelerate until the desired resin compaction. Depending on the rigidity of the resin a 5-15 psi pressure rise above the normal operating pressure at high flow rate, may be tolerated (less for soft resin and more for rigid resins). Stop the pump! The column is now packed. Next, close the column inlet and outlet valves.

e) Inflate the Slurry Packing Seal and close the Packing Seal Inflation valve.

f) Disconnect slurry line from column outlet and run buffer through the line back into the resin beaker and clear the line.

g) Next connect pump to the top of the column and connect the outlet to the slurry container and open column inlet/outlet valves. Run buffer through the bed and excess resin lodged between the bottom frit and column outlet will now get dislodged and exit the bottom into the slurry container. When no more resin is detected, stop the flow by turning off the pump.

h) Run the column in the forward and reverse direction at max flow for 3-5 bed volumes to condition the bed.

i) The column is now ready for packing integrity test and operation.

FIG. 7 illustrates a chromatography-column with one or more inflation/deflation packing seals being packed with resin. The column may be run in either the traditional down-flow mode by connecting the inlet of the column to the buffer via a pump and pressure gauge as shown in FIG. 7 or in the up-flow mode by reversing the pump connection to the bottom. The pressure gauge is used to ensure that the pressure does not exceed the operating pressure of the resin and column and the bubble trap to prevent accidental air intrusion into the column (can cause channels in the resin bed). The seals 702 block or unblock the path.

The running flow rate is determined by following either the manufacturer's suggested linear velocity/specific velocity (bed volumes/min or /hr) or the empirically determined residence time e.g. a residence time of 2 min=0.5 bed volume/min flow-rate, necessary for the separation.

The columns offer benefits including the ease to pack the radial columns; the ease to pack the axial columns; a simplified method for slurry packing and unpacking of radial and axial columns; a manual or automated skid or system for packing and unpacking radial and axial columns; and many other benefits.

The radial columns envisaged vertical packing through packing ports located above or below bed. Also, the packing direction was orthogonal to direction of flow while running the column.

The radial columns may also have packing is in the same direction as when running the column. The columns make dead resin which is not cleanable is below the resin bed and is hard to dislodge more easy to clean.

The axial columns with retractable valves cause higher density packing in the center of the column around the packing port (i.e.) the packing is more tightly packed. In circumferential packing as shown with the inflatable seal in this invention, the packing pressure distribution is more homogeneous on the column perimeter where increasingly more volume of resin resides and thus uniform resin packing density is critical. With greater entrance and exit area, the column is easier and faster to reproducibly pack and un-pack. Performance is also enhanced.

The chromatography column packs and unpacks using the inlet and outlet operating ports via an inflatable seal. The inflatable seals serve the purpose of resin slurry entry or egress within the column and then during operation expand to direct the flow of the product of interest through the resin. The path for inflate seal and resin is naturally flushed out without the need for a separate line or port to accomplish this.

While some specific embodiments of the invention have been shown the invention is not to be limited to these embodiments. For example, the specific piping flow routes may be routed in parallel or have other modifications. The invention is to be understood as not limited by the specific embodiments described herein, but only by scope of the appended claims.

What is claimed is:

1. An apparatus, comprising:
a chromatography-column having one or more inflatable seals, a first port, and a second port to facilitate packing and unpacking resin in the chromatography-column, where the packing and unpacking of the resin in the chromatography column is designed to occur using the first port and the second port and controlling an inflation state of the one or more inflatable seals, where the same two ports are also used during a normal operation of the chromatography-column by running 1) a product of interest in from a bioreactor, 2) a protein solution from another tank, or 3) a synthetic product of interest from said another tank, or 4) any of these through these two ports to have the resin packed in the chromatography column filter of the product of interest, where the one or more inflatable seals within the chromatography-column block or unblock a pathway to a resin bed in the chromatography-column and where the chromatography-column is a radial-flow chromatography-column that includes an inlet port as the first port, an outlet packing-and-running port located at a bottom of the chromatography-column for easy drainability as the second port, the one or more inflatable seals, each seal with a seal fluid line and seal valve, a body and outer shell of the column, an inner screen, a resin bed chamber located between the inner screen and the outer shell of the column, and an air vent coupled to the resin bed chamber.

* * * * *